United States Patent
Chu

(10) Patent No.: US 7,220,553 B2
(45) Date of Patent: May 22, 2007

(54) USE OF RUSSELL'S VIPER VENOM-INDUCED PLASMA FACTOR XA ACTIVITY TO MONITOR THE ACTIVITY OF FACTOR XA INHIBITORS

(75) Inventor: Valeria Fung-Hwei Chu, Belle Mead, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/125,627

(22) Filed: Apr. 18, 2002

(65) Prior Publication Data

US 2003/0049704 A1    Mar. 13, 2003

Related U.S. Application Data

(63) Continuation of application No. PCT/EP00/10646, filed on Oct. 28, 1999.

(60) Provisional application No. 60/163,161, filed on Nov. 2, 1999.

(30) Foreign Application Priority Data

Dec. 23, 1999 (GB) ................................. 9930535.1

(51) Int. Cl.
*G01N 33/54* (2006.01)

(52) U.S. Cl. ...................... 435/7.1; 435/6; 435/69.1; 435/13; 436/69; 436/93; 436/94; 436/127; 436/129

(58) Field of Classification Search .................. 435/7.1, 435/6, 69.1, 13; 436/69, 93, 94, 111, 127, 436/129
See application file for complete search history.

(56) References Cited

U.S. PATENT DOCUMENTS

| 4,946,755 | A | * | 8/1990 | Yin .............................. 435/13 |
| 4,946,775 | A | | 8/1990 | Yin |
| 5,187,155 | A | * | 2/1993 | Fair ............................ 214/12 |
| 5,886,191 | A | * | 3/1999 | Dominguez et al. ........ 548/491 |
| 6,103,888 | A | * | 8/2000 | Larrick et al. ............. 536/23.5 |

FOREIGN PATENT DOCUMENTS

| WO | WO 97/24118 | | 7/1997 |
| WO | WO 9724118 | * | 7/1997 |

OTHER PUBLICATIONS

Hara et al. Thrombosis Research 1995 vol. 80, p. 99-104.*

* cited by examiner

*Primary Examiner*—Long V. Le
*Assistant Examiner*—Jacob Cheu
(74) *Attorney, Agent, or Firm*—George G. Wang; Joseph D. Rossi; Jiang Lin

(57) ABSTRACT

The invention relates to a method of monitoring the effect of a direct of indirect Factor Xa inhibitors comprising the steps of collecting a plasma sample from a patient, adding a solution of Russell's viper venom to the plasma sample and measuring the clotting time or the residual FXa activity chromogenically.

8 Claims, No Drawings

USE OF RUSSELL'S VIPER VENOM-INDUCED PLASMA FACTOR XA ACTIVITY TO MONITOR THE ACTIVITY OF FACTOR XA INHIBITORS

This invention is directed to measuring Factor Xa activity. Such activity can be measured using blood clotting time or chromogenic substrates. The instant invention concerns assay methods for measuring the activity of FXa inhibitors. More particularly, the present invention concerns the use of Russell's viper venom (hereinafter "RVV-X") to induce the individual's endogenous FXa activity and measure the effect of FXa inhibitors. The methods for measuring FXa activity in plasma are by clotting time and by chromogenic methodology.

The publication (Clinical Chemistry, 26/7, pages 885–890, 1980) discloses an assay for factor X in which factor X is activated directly by Russel's viper venom, in Alcohol (Vol. 13, No. 6, pages 539–545, 1996) the effect of acetaldehyde upon factor X and factor Xa is described. In a case report an IgG is described which bounds to the light chain of intact factor X and thus inhibits the activation of factor X (Thrombosis & Haemostasis (72(3), pages 363–371, 1994).

Assays such as APTT and PT have been used before to measure blood clotting time. Such assays, however, are not sensitive to detect dosage differences in administration of direct Factor Xa (hereinafter "FXa") inhibitors. The present invention addresses the problem of monitoring the safety and efficacy of direct FXa inhibitors. The methods of the present invention can be used in all species for monitoring the safety and efficacy of intravenous or orally active FXa inhibitors. It is believed the methods of the present invention could also be used to measure the safety and efficacy of thrombin inhibitors and indirect FXa inhibitors such as anticoagulants for factors upstream of the coagulation cascade and heparin, more particularly low molecular weight heparin. The methods could be used for predicting the prothrombotic state of a patient. In the endeavor to provide improved assay methods for measuring the activity of FXa inhibitors, it has now been found that the same can be achieved by the use of Russell's viper venom (hereinafter "RW-X") to measure prolongation of clotting time produced by the activity of FXa inhibitors.

The invention, as it is explained in the claims, achieves the object by a method of monitoring the effect of Factor Xa inhibitors comprising the steps of:
  a) collecting a plasma sample from a patient, who has received a FXa inhibitor, an anticoagulant, an antithrombotic agent, or any combination thereof,
  b) adding a solution of Russell's viper venom to the plasma sample and
  c) measuring clotting time or a chromogenic change.

Another object of the invention is a method of monitoring the effect of Factor Xa inhibitors comprising the steps of:
  a) collecting a plasma sample from a mammal,
  b) providing Factor X deficient plasma sample of the same species to be used to make serial dilutions of the normal plasma sample,
  c) adding a solution of Russell's viper venom to the plasma samples defined in a) and b),
  d) comparing the clotting time measured for the plasma sample from a mammal with the clotting time measured for the plasma samples diluted with Factor X deficient plasma,
  e) constructing a standard curve of % FXa activity (proportional to the normal plasma content) and measuring clotting time prolongation,
  f) knowing the clotting time of an individual, who has received FXa inhibitor treatment, and obtaining the % residual FXa activity or % FXa inhibition from the standard curve.

Another object of the invention is a method of monitoring the effect of Factor Xa inhibitors comprising the steps of:
  a) collecting a plasma sample from a mammal that has received an FXa inhibitor;
  b) dividing said plasma sample into portions, saving one portion as the control normal plasma and adding serial dilutions of Factor Xa inhibitor to other portions;
  c) adding a solution of Russell's viper venom to plasma samples defined in b);
  d) comparing the clotting time measured for the plasma sample without Factor Xa inhibitor with that plasma samples with added Factor Xa inhibitor; and
  e) constructing a dose-dependent clotting time prolongation curve and determining the concentration of a FXa inhibitor required to prolong the clotting time twice longer than the control plasma clotting time.

A mammal is a human being or an animal such as cattle, sheep, rabbit, mouse or rat. A Factor Xa inhibitor is a compound which is an inhibitor of the blood clotting enzymes, especially factor Xa. The term "patient" means a human or a mammal.

Another object of the invention is a method of monitoring the effect of Factor Xa inhibitors comprising the steps of:
  a) collecting a plasma sample from a mammal that has received an FXa inhibitor;
  b) dividing said plasma sample into portions, saving one portion as the control plasma and adding serial dilutions of Factor Xa inhibitor to other portions;
  c) adding a solution of Russell's viper venom (RVV-X) to plasma samples defined in b);
  d) comparing the FXa activity measured for the control plasma sample with the residual FXa activity measured for the plasma samples with added Factor Xa inhibitor;
  e) constructing a standard curve of dose-dependent inhibition of RVV-X induced by FXa inhibitor; and
  f) estimating the concentration of FXa inhibitor by using the standard curve.

Another object of the invention is to reduce or minimize variations in measurement of the clotting time due to the handling of the plasma samples. This is achieved by adding cephalin to the plasma samples. A preferred cephalin source is from rabbit brain. A preferred chromogenic compound for determining the FXa activity is Spectrozyme Fxa®. Other FXa chromogenic substrates can also be used. The method according to the invention is preferably performed in a buffer having a pH from 7 to 8. A preferred buffer is a tris(hydroxymethyl)aminomethan buffer (Tris), containing sodium chloride (NaCl) and polyethylene glycol-8000 (PEG-8000). Preferred concentrations are from 10 mM to 200 mM, from 20 mM to 600 mM, and from 0.02% to 1% for Tris, NaCl, and PEG-8000, respectively.

Another object of the invention is a method of monitoring the effect of FXa (FXa) inhibitors treatment comprising the steps of:
  a) collecting a plasma sample from a mammal that has received an FXa inhibitor;
  b) dividing said plasma sample into portions, saving one portion as the control plasma and adding serial dilutions of FXa inhibitor to other portions;
  c) adding a solution of Russell's viper venom (RVV-X) to plasma samples defined in b);
  d) comparing FXa activity measured for the control plasma with the residual FXa activity measured for the plasma samples with added FXa inhibitor;
  e) constructing a standard curve of dose-dependent inhibition of RVV-X induced by FXa inhibitor; and f) estimating the concentration of FXa inhibitor at various points in time during the FXa inhibitor treatment by using the standard curve.

Another object of the invention is a method of monitoring the effect of Factor Xa (FXa) inhibitors treatment comprising the steps of:
a) collecting a plasma sample from a mammal that has received an FXa inhibitor;
b) dividing said plasma sample into portions, saving one portion as the control plasma and adding serial dilutions of FXa inhibitor to other portions;
c) adding a solution of Russell's viper venom to plasma samples defined in b);
d) comparing the clotting time measured for the control plasma with that of the plasma samples with added FXa inhibitor; and
e) constructing a dose-dependent clotting time prolongation curve and determining the concentration of a FXa inhibitor required to prolong the clotting time twice longer than the control plasma clotting time.

Another object of the invention is to provide a kit for using the method according to the invention for a diagnostic assay for FXa inhibitor determination.

Another object of the invention is the use of the method according to the invention for measuring the activity of a Factor Xa inhibitor. A particularly preferred Fxa inhibitor is methyl-3-(4'-N-oxopyridylphenoyl)-3-methyl-2-(m-amidinobenzyl)-propionate.

In the examples it is shown that the RVVT protocol, is useful for measuring RVV-X induced FXa activity in plasma by clotting time. The second protocol, the RVVC protocol, is useful for measuring RVV-X induced FXa activity in plasma by chromogenic methodology. RVVT showed dose-dependent prolongation of clotting time by FXa inhibitors. RVVC showed dose-dependent FXa inhibition by FXa inhibitors. Both methods were successfully used to discriminate varying concentrations of FXa inhibitors in ex vivo plasma samples taken from human patients.

The method according to the invention is described in detail in the examples which follow

EXAMPLE 1

| Russell's viper venom-induced Clotting Time (RVVT) Protocol | |
|---|---|
| Reagents: | |
| FXa buffer: | 0.05 M Tris, 0.15 M NaCl, 0.1% PEG-8000, pH7.5 add 6.06 g Tris, 8.77 g NaCl, 1.0 g PEG-8000 to 800 mL H$_2$O adjust pH to pH 7.5 using concentrated HCl. Fill up to 1 L with H$_2$O |
| RVV-X: | Enzyme Research Lab. Dilute to 1 mg/ml with FXa buffer then 1/400 in the same buffer. |
| RVV-X working solution (RVV-Ca): | 2 ml of 1/400 RVV-X + 18 ml of 0.0035 M CaCl$_2$. Concentration of RVV-X at this point is 0.25 µg/ml. |
| FX-deficient plasma | American Diagnostica Inc. |
| Procedure: | All the reagents should be kept at 4° C. (on ice-water mixture), before use. |
| Standard | 1. Make 2-fold serial dilutions of normal pooled plasma or patient's plasma with FX-deficient plasma from 1~1/256 |
| | 2. Add 0.2 ml FXa buffer, 0.1 ml plasma dilution to the cuvette then 0.1 ml of RVV-Ca (MLA-800 clotter add this reagent automatically). |
| | 3. Measure clotting time. |
| | 4. Construct standard curve. |

Dose-dependent clotting time prolongation curve from the compound methyl-3-(4'-N-oxopyridylphenoyl)-3-methyl-2-(m-amidinobenzyl)-propionate (hereinafter "RPR") or the trifluoroacetate salt of RPR:
1. Add 0.1 ml FXa buffer, 0.1 ml serial dilution of RPR, 0.1 ml normal pooled or patients plasma to the cuvette then 0.1 ml of RVV-Ca (MLA-800 dotter add this reagent automatically).
2. Measure clotting time.
3. Construct the dose-dependent clotting time prolongation curve.
4. Calculate concentration for 2×RVVT

EXAMPLE 2

Russell's Viper Venom-induced FXa in Plasma Measured Chromogenically (RVVC)

Protocol

RVVC ASSAY

RVV-induced FXa activity in plasma measured chromogenically.

A) Reagents

PEG-Ca++buffer: 0.05M Tris, 0.15M NaCl, 0.01 M CaCl$_2$, 0.1% PEG-8000, pH 7.50 Add 6.06 g Tris, 8.77 g NaCl, 1 g PEG-8000, 1.47 g CaCl$_2$. 2 H$_2$O to 800 ml H$_2$O adjust to pH 7.5 using concentrated HCl, fill up to 1 L with H$_2$O RVV-X Add 44 µl of PEG-Ca$^{++}$ buffer to 50 µl of RVV-X (Russell's' Viper Venom): stock (Enzyme Research Labs, 1.88 mg/ml) to prepare 1 mg/ml solution, keep on ice at all times. Dilute 1 mg/ml stock to ¹/₁₀→¹/₁₀→¼ (=¹/₄₀₀). Dilutions are made in PEG-CAE Buffer.

Substrate Spectrozyme Dissolve 50µ mole of Spectozyme FXa, American

FXa®: Diagnostic, in 5 ml sterile water to make a 10 mM stock solution.

Spectrozyme FXa®1.6 mM Add 0.8 ml of 10 mM stock to 4.2 ml of PEG-Ca working solution: buffer.

B) Procedure:
1. Add the reagents to the microtiter plates or test tubes in the following order:

| Reagent | Sample | Control 1 | Control 2 |
|---|---|---|---|
| 1. PEG-Ca$^{++}$ buffer | 120 µl | 120 µl | 145 µl |
| 2. control plasma | — | 5 µl | 5 µl |
| 3. clinical samples (plasma) | 5 µl | — | — |
| 4. Spectrozyme FXa ® 1.6 mM | 50 µl | 50 µl | 50 µl |
| 5. RVV-X (1 mg/ml) 1/400 dilution | 25 µl | 25 µl | — |

2. Follow the reaction kinetically for 5 min.

C) Calculation:

Measure the initial velocity, however, ignore the lag phase. In general measure the initial rate of the linear portion of the time course.

Use initial rates of clinical samples at different time points and then compared to the pre-dosing control to calculate % inhibition.

Various concentrations of the compound RPR spiked in plasma were assayed for PT, APTT and PVVT prolongation. The results in Table 1 suggest that RVVT is the most sensitive indicator among the three clotting time assays for the effect of the compound RPR, as a FXa inhibitor.

RVV-X induced clotting time (RVVT) assay could be conveniently used for monitoring the effect of RPR on patient's endogenous plasma FXa.

TABLE 1

| Test system | Effect of RPR on fold-change Concentration of RPR (µg/ml) | | |
|---|---|---|---|
| | 50 µg/ml | 166 µg/ml | 322 µg/ml |
| RVVT | 1.33 | 2.66 | 4.41 |
| PT | 1.08 | 1.16 | 1.25 |
| APTT | 1.08 | 1.41 | 1.5 |

EXAMPLE 3

Russell's Viper Venom-induced Clotting Time (RVVT) Protocol (II)

Reagents:

FXa buffer: 0.05M Tris, 0.15M NaCl, 0.1% PEG-8000, pH7.5 add 6.06 g Tris, 8.77 g NaCl, 1.0 g PEG-8000 to 800 mL $H_2O$ adjust to pH 7.5 using ~2 ml of concentrated HCl. fill up to 1 L with $H_2O$ RVV-X: Enzyme Research Lab. Dilute to 1 mg/ml with FXa buffer then 1/200 in the same buffer. 2 ml of 1/200 RVV-X+18 ml of 0.035 M $CaCl_2$, final concentration of RVV-X at this point is 0.5 µg/ml.

Rabbit brain Centerchem

Cephalin Reconstitute with 3.125 ml of 0.035 M $CaCl_2$ in FXa buffer to a final concentration of 1.6 mg/ml.

RVV-X RB Equal volume of 0.5 µg/ml RVV-X mixed with equal volume of

Cephalin working 1.6 mg/ml of rabbit brain Cephalin.

solution The final concentrations of RVV-X and Cephalin in the reagent (RVV-Ca-reservoir at this stage are 0.25 µg/ml and 0.8 mg/ml, Cephalin): respectively.

Procedure: All the reagents should be kept at 40° C. (on ice-water mixture), before use.

Predose plasma 1. Add 0.2 ml FXa buffer, 0.1 ml predose plasma to the cuvette normal RVVT then 0.1 ml of RVV-Ca-Cephalin. (Final concentrations of RVV-X and Cephalin are 0.0625 µg/ml and 0.2 mg/ml, respectively)

2 Measure clotting time.

Result: Calculate fold-change of RVVT

Effect of rabbit brain cephalin on RVVT

RVV-induced plasma (Pooled GK plasma and donors DN, RB, TD) clotting time with added dilutions of cephalin (n=2)

| Final concentration of rabbit brain cephalin (mg/ml) | Clotting time (sec) | | | |
|---|---|---|---|---|
| | pooled GeorgeKing plasma (# 99X1) | plasma DN | plasma RB | plasma TD |
| 0 | 28.9 | 55.1 | 65.3 | 86.4 |
| 0.0049 | 28.4 | 40.9 | 44.3 | 52.5 |
| 0.0098 | 28.5 | 38.1 | 39.5 | 47.1 |
| 0.0195 | 27.1 | 33.4 | 33.2 | 39.1 |
| 0.039 | 25.5 | 29.9 | 28.9 | 33.9 |
| 0.078 | 24.7 | 27.7 | 26.4 | 31.6 |
| 0.156 | 25.1 | 27.4 | 25.3 | 29.8 |
| 0.312 | 27.2 | 30.4 | 26.1 | 31.6 |

Conclusion: RVVT variations due to the sample handling could be reduced by addition of ~0.2 mg/ml of rabbit brain cephalin in the reaction mixture.

What is claimed is:

1. A method of monitoring the effect of Factor Xa (FXa) inhibitors treatment comprising the steps of:
   a) collecting a plasma sample from a mammal that has received an FXa inhibitor;
   b) dividing said plasma sample into portions, saving one portion as the control plasma and adding serial dilutions of FXa inhibitor to other portions;
   c) adding a solution of Russell's viper venom (RVV-X) to plasma samples defined in b);
   d) comparing FXa activity measured for the control plasma with the residual FXa activity measured for the plasma samples with added FXa inhibitor;
   e) constructing a standard curve of dose-dependent inhibition of RVV-X induced by FXa inhibitor; and
   f) estimating the concentration of FXa inhibitor at various points in time during the FXa inhibitor treatment by using the standard curve.

2. A method of monitoring the effect of (FXa) inhibitors treatment comprising the steps of:
   a) collecting a plasma sample from a mammal that has received an FXa inhibitor;
   b) dividing said plasma sample into portions, saving one portion as the control plasma and adding serial dilutions of FXa inhibitor to other portions;
   c) adding a solution of Russell's viper Venom to plasma samples defined in b);
   d) comparing the clotting time measured for the control plasma with that of the plasma samples with added FXa inhibitor; and
   e) constructing a dose-dependent clotting time prolongation curve and determining the concentration of a FXa inhibitor required to prolong the clotting time twice longer than the control plasma clotting time.

3. The method according to any of claims 1 to 2, wherein the residual FXa activity is measured chromogenically.

4. The method of claim 1 wherein cephalin is added to the plasma samples.

5. The method according to claim 1 or 4 wherein the plasma samples where incubated in a buffer having a pH from 7 to 8.

6. The method according to claim 1 or 5 wherein the plasma sample is collected from a patient who has received an anticoagulant or an antithronibotic agent or a combination thereof in addition to the FXa inhibitor.

7. The method of claim 1 wherein said method being used in manufacturing a diagnostic assay kit for monitoring the level of FXa inhibition by an inhibitor in a mammal.

8. The method of claim 1 wherein said method being used in determination of the effects of a direct or an indirect (FXa) inhibitor on a mammal.

* * * * *